US010211029B1

(12) United States Patent
Heinrich

(10) Patent No.: US 10,211,029 B1
(45) Date of Patent: Feb. 19, 2019

(54) ACOUSTIC MANIPULATION OF PLASMA FOR ARBITRARY PLASMA METAMATERIAL FORMATION

(71) Applicant: Lockheed Martin Corporation, Bethesda, MD (US)

(72) Inventor: Jonathon R. Heinrich, Palmdale, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 15/867,228

(22) Filed: Jan. 10, 2018

(51) Int. Cl.
| H05H 1/36 | (2006.01) |
| H05H 1/46 | (2006.01) |
| H05H 1/48 | (2006.01) |
| H05G 2/00 | (2006.01) |
| H01Q 1/36 | (2006.01) |
| G03F 7/20 | (2006.01) |
| H01J 37/32 | (2006.01) |
| H01J 37/24 | (2006.01) |

(52) U.S. Cl.
CPC ........ *H01J 37/32082* (2013.01); *H01J 37/24* (2013.01); *H01J 37/3244* (2013.01); *H01J 37/32816* (2013.01); *H01J 2237/332* (2013.01)

(58) Field of Classification Search
None
See application file for complete search history.

(56) References Cited

U.S. PATENT DOCUMENTS

| 4,983,189 A | 1/1991 | Peterson et al. |
| 5,277,740 A | 1/1994 | Yoneda |
| 5,367,139 A * | 11/1994 | Bennett ................. C23C 16/44 156/345.44 |
| 7,601,267 B2 | 10/2009 | Haske et al. |
| 8,378,877 B2 | 2/2013 | Tishin et al. |
| 8,803,637 B1 | 8/2014 | Peralta et al. |
| 9,130,250 B2 | 9/2015 | Kitaoka et al. |
| 2011/0199273 A1 | 8/2011 | Kim et al. |
| 2016/0208213 A1* | 7/2016 | Doyle .................. B06B 1/0269 |

FOREIGN PATENT DOCUMENTS

WO    2016096144    12/2015

OTHER PUBLICATIONS

Mitri,Farid, Sinha, Dipen, "Creating a nanocomposite metamaterial structure using the radiation force of ultrasound standing waves." IEEE International Ultrasonics Symposium Proceedings, 2011, pp. 1556-1558.

* cited by examiner

*Primary Examiner* — Dedei K Hammond
(74) *Attorney, Agent, or Firm* — Baker Botts L.L.P.

(57) ABSTRACT

A method for producing a steady-state three dimensional shape in a plasma includes filling a space with a gas, ionizing the gas with a radio frequency source to form a plasma, and directing acoustic waves into the plasma from a plurality of acoustic sources. The acoustic waves from each of the plurality of acoustic sources interact to create standing wave pattern forming a three dimensional shape in the plasma.

18 Claims, 6 Drawing Sheets

ACOUSTIC MANIPULATION OF PLASMA FOR ARBITRARY PLASMA METAMATERIAL FORMATION

TECHNICAL FIELD OF THE INVENTION

This invention relates generally to manipulation of plasma using acoustics.

BACKGROUND

Plasmas are ionized gases that may be created by a variety of methods. One way of creating plasmas is by using electromagnetic energy to ionize a gas. Plasmas may conduct electricity and interact with electromagnetic radiation. Acoustic sources produce pressure waves in a medium through which acoustic waves travel, such as a solid, liquid, or gas. These pressure waves may change the local density of the material through which the acoustic waves travel.

Metamaterials are manmade materials having properties not normally found in nature. For example, some metamaterials display a negative index of refraction. Many metamaterials are constructed from multiple elements of composite materials arranged in a repeating pattern or structure. The elements of a metamaterial are generally smaller than the wavelength of the phenomena a metamaterial influences. For example, a metamaterial acting as an optical wave guide may have a pattern made of elements smaller than the wavelength of light which interacts with the metamaterial.

SUMMARY

According to some embodiments, apparatus for producing a plasma having a three dimensional shape includes a chamber filled with a gas, an energy source operable to provide energy to ionize the gas in the chamber to form a plasma, a plurality of sensors operable to measure one or more properties of the plasma, and a plurality of acoustic sources capable of producing acoustic waves. The acoustic waves produced by each of the plurality of acoustic sources may interact to create a standing wave pattern forming a three dimensional shape in the plasma.

According to some embodiments, a method is provided for producing a steady-state three dimensional shape in a plasma. The method comprises filling a space with a gas, ionizing the gas with a radio frequency source to form a plasma, and directing acoustic waves into the plasma from a plurality of acoustic sources. The acoustic waves from each of the plurality of acoustic sources may interact to form a standing wave pattern having a three dimensional shape in the plasma.

According to some embodiments, a plasma may be held in a shape by acoustic waves generated by a plurality of acoustic sources. The acoustic waves generated by each of the plurality of acoustic sources may interact with acoustic waves produced by others of the plurality of acoustic sources to produce a first plurality of areas having a higher density than a second plurality of areas.

Technical advantages of certain embodiments may include creating a plasma with properties of a metamaterial that may replace solid metamaterials in certain applications. Additionally, certain embodiments may include creating a plasma that may be formed into a varying metamaterial, allowing the properties of the plasma metamaterial to be varied in time and space. In certain embodiments, a plasma may be formed into an arbitrary three dimensional shape. Such a shape may be placed in contact with a complex object to apply a coating or to etch certain areas of the object, in some embodiments.

BRIEF DESCRIPTION OF THE DRAWINGS

To provide a more complete understanding of the present invention and the features and advantages thereof, reference is made to the following description taken in conjunction with the accompanying drawings, in which.

DETAILED DESCRIPTION OF THE DRAWINGS

Embodiments of the present invention and its advantages are best understood by referring to FIGS. 1 through 4 of the drawings, like numerals being used for like and corresponding parts of the various drawings.

Acoustic waves applied to gases may change the pressure and density of gases in localized areas. By applying acoustic waves from more than one source, a standing wave pattern may be created in the gas, due to interactions between the acoustic waves, forming areas of higher pressure and density and lower pressure and density. In some embodiments, the acoustic waves may be high intensity ultrasonic waves. In other embodiments, the acoustic waves may be audible to the human ear. In other embodiments, the acoustic waves may be infrasonic acoustic waves, having a frequency lower than the human ear can detect. In some embodiments, the acoustic waves may have any frequency and any intensity.

A plasma is an ionized gas. The charge density of a plasma is dependent upon the background neutral pressure of the gas and the coupling of the input energy. Areas of different neutral pressure may have different plasma densities. In some embodiments, areas or increased neutral density may have increased plasma density. In other embodiments areas of decreased neutral density may have increased plasma density. The operational regime may be determined by one or more of the neutral-electron mean free path, the electron-ion recombination length, and the ion-neutral mean free path.

Figure 1:
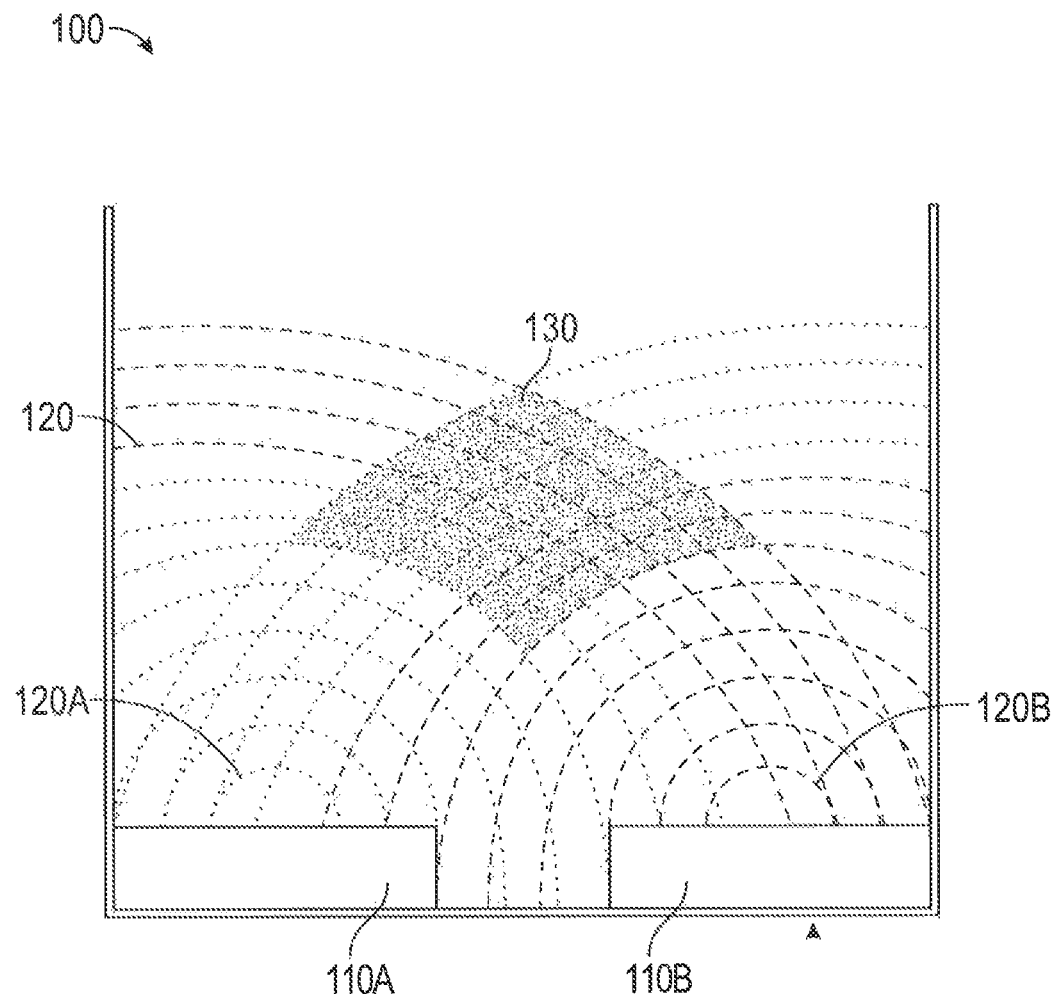
FIG. 1 a plasma shaped in two dimensions by acoustic waves, according to certain embodiments.

FIG. 1 illustrates a plasma shaped in two dimensions by acoustic waves, according to certain embodiments. In the illustrated embodiment, acoustic sources 110 produce acoustic waves 120. In some embodiments, acoustic waves 120 may be high intensity ultrasonic waves. In other embodiments, acoustic waves 120 may be audible to the human ear. In other embodiments, acoustic waves 120 may be infrasonic acoustic waves, having a frequency lower than the human ear can detect. In some embodiments, acoustic waves 120 may have any frequency and any intensity.

Acoustic waves 120A produced by acoustic source 110A may interact with acoustic waves 120B produced by acoustic source 110B. Interaction between acoustic waves 120A and acoustic waves 120B may create density fluctuations in a fluid, such as a gas or plasma, through which acoustic waves 120A and 120B propagate. In some embodiments, interaction between acoustic waves 120A and acoustic waves 120B may create a standing wave pattern with areas having higher density and areas having lower density in the fluid through which the acoustic waves 120 pass. These areas of higher density and lower density may be configured by adjusting acoustic waves 120A and acoustic waves 120B produced, respectively, by acoustic source 110A and acoustic source 110B. Configuration of the high density areas and low density areas may allow a gas or plasma to be fashioned into a shape, with a greater amount of plasma in regions determined by the neutral pressure profile. For example, a higher density areas plasma 130 may be configured to have a shape as shown in FIG. 1 by an interaction between acoustic waves 120A and acoustic waves 120B.

In some embodiments, any number of acoustic sources may be used to produce acoustic waves. A greater number of acoustic sources 110 may allow for more complex shapes to be created by enabling complex interactions between acoustic waves 120 produced by multiple acoustic sources 110. FIG. 1 illustrates an embodiment in two dimensions, with two acoustic sources in the plane illustrated. However, it should be noted that acoustic waves propagate in three dimensions in a fluid, and the shape of plasma 130 may be affected by acoustic waves produced by acoustic sources not shown in FIG. 1. For example, acoustic sources located above or below plane illustrated by FIG. 1 may affect the shape of plasma 130.

In some embodiments, acoustic sources 110 may be variable so as to produce variable acoustic waves 120. Acoustic sources 110 may be capable varying the frequency and amplitude of acoustic waves 120. Varying acoustic waves 120 may cause the standing wave pattern created by the interaction of acoustic waves 120 to change, thereby causing the shape of plasma 130 to change. By controlling acoustic waves 120 they shape of plasma 130 may be controlled.

Figure 2A:
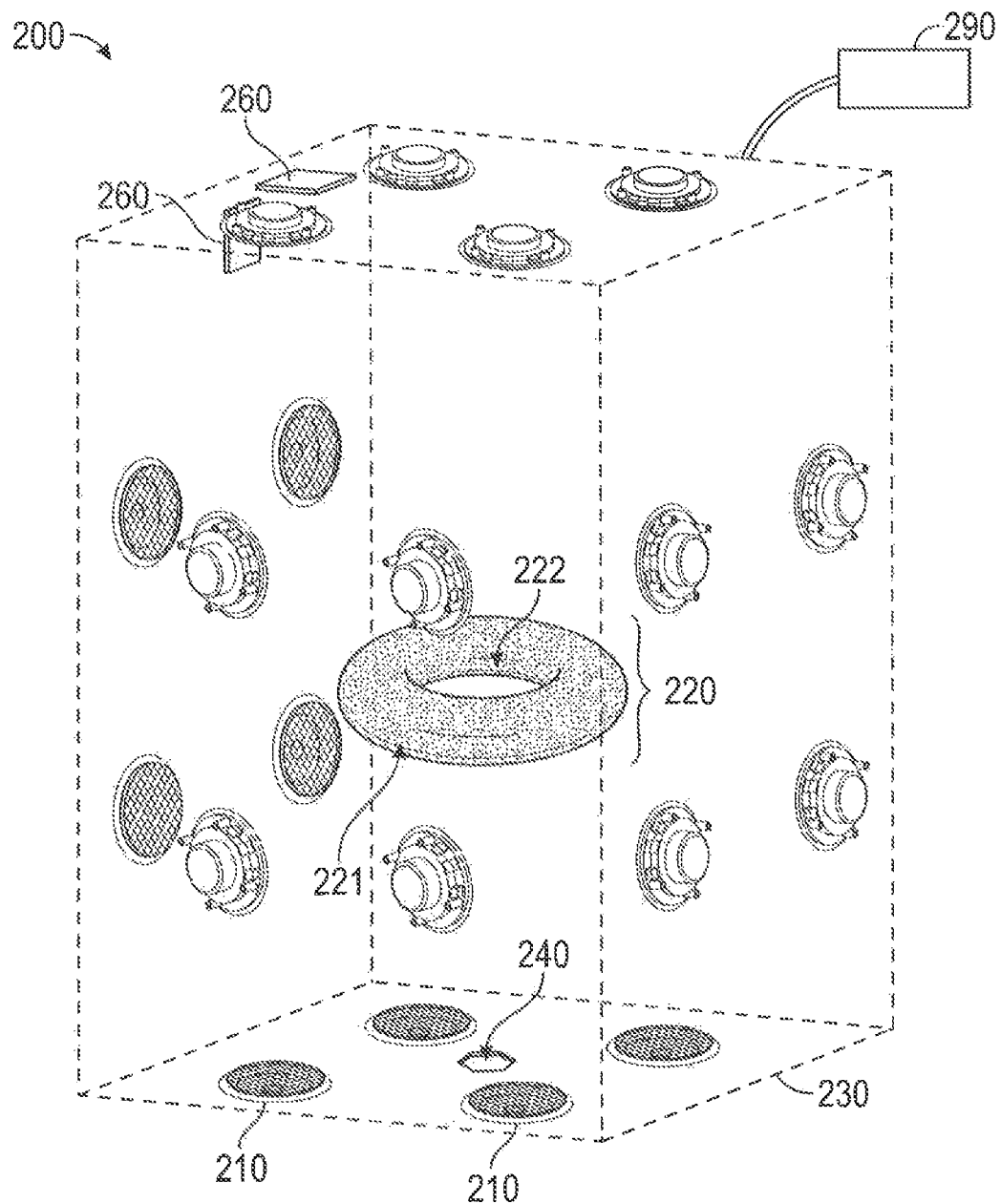
FIG. 2A illustrates a plasma shaped in three dimensions by acoustic waves and an apparatus for forming and shaping the plasma, according to certain embodiments.

FIG. 2A illustrates a plasma shaped in three dimensions by acoustic waves and an apparatus 200 for shaping the plasma, according to certain embodiments. In a similar manner to the embodiment illustrated by FIG. 1, acoustic sources 210 produce acoustic waves, similar to acoustic waves 120. Acoustic waves are not illustrated in FIG. 2A for simplicity. In some embodiments, the acoustic waves may be high intensity ultrasonic waves. In other embodiments, the acoustic waves may be audible the human ear. In other embodiments, the acoustic waves may be infrasonic acoustic waves, having a frequency lower than the human ear can detect. In some embodiments, the acoustic waves may have any frequency and any intensity.

Acoustic waves produced by each acoustic source 210 may interact, resulting in a standing wave pattern with areas of higher density and lower density. These interactions may be used to shape a fluid, such as a gas or a plasma. In the illustrated embodiment, a plasma 220 is shaped into a torus by acoustic waves produced by acoustic sources 210. In other embodiments, plasma 220 may be shaped into any shape by acoustic waves produced by acoustic sources 210. Areas of high plasma density 221 and areas of low plasma density 222 may result from interactions of acoustic waves produced by acoustic sources 210. In some embodiments, the density of plasma 220 may be continuously variable throughout plasma 220 according to interactions between acoustic waves produced by acoustic sources 210. In certain embodiments, areas of low plasma density 222 may have a density so low as to be negligible (e.g., resulting in a permittivity very close to vacuum permittivity for a specified frequency).

In some embodiments, acoustic sources 210 may be affixed to the interior of a chamber 230. Chamber 230 may have any shape and may contain plasma 220. Chamber 230 may also have an energy source 240. Energy source 240 may provide energy to ionize a gas contained in chamber 230, resulting in a plasma 220. In some embodiments, energy source 240 may be a radio frequency (RF) source. In other embodiments, energy source 240 may be a high power microwave source. In other embodiments, energy source 240 may be an electron beam. In some embodiments, chamber 230 may have more than one energy source 240.

In some embodiments, chamber 230 may include a computer system 290 that controls the shaping of plasma 220 by providing instructions to the elements of chamber 230, such as acoustic sources 210 and energy source 240. In some embodiments, computer system 290 may provide instructions based on inputs computer 290 receives from sensors 260 located on or in chamber 230. Sensor 260 may include any type of sensor, including but not limited to temperature sensors, acoustic sensors, visible light sensors or cameras, capacitive sensors, inductive sensors, pressure sensors, or any other type of sensor. Computer system 290 may be either external to chamber 230 or incorporated into chamber 230. Certain embodiments of computer system 290 are discussed in more detail below with respect to FIG. 3.

In some embodiments, the interior of chamber 230 may be held at a pressure greater than or equal to 1 millitorr (mTorr), and less than or equal to 1000 torr. In some embodiments, plasma 220 contained in chamber 230 may have a density high enough to sufficiently modify the permittivity for a given electromagnetic frequency as compared to vacuum permittivity.

Plasma 220 may be shaped into a metamaterial by interaction of acoustic waves from acoustic sources 210, in some embodiments. Metamaterial plasma 220 may be shaped to have a repeating pattern or structure that effects how non-ionizing electromagnetic radiation interacts with plasma 220. Metamaterial plasma 220 may be a three dimensional metamaterial having a pattern or structure that repeats in three dimensions. In some embodiments, a three dimensional metamaterial plasma 220 have a pattern or structure that varies between each axis of its three dimensional structure. For example, a plasma metamaterial could be created by shaping plasma 220 to interact with certain frequencies of electromagnetic radiation, such as microwaves or radio waves. Examples of interactions between non-ionizing electromagnetic radiation and plasma 220 that may be desirable include shaping plasma 220 to bend, focus, or steer radio waves. Other examples of interactions between non-ionizing electromagnetic radiation and plasma 220 that may be desirable include shaping plasma 220 to act as a filter to pass only certain frequencies of electromagnetic waves, or to act as a prism to split apart different frequencies of electromagnetic waves. In certain embodiments, plasma 220 may be shaped to have properties similar to a photonic crystal, which may enable plasma 220 to be used as a waveguide or as the whole or a portion of a nonlinear optical device.

In some embodiments, the properties of plasma 220 shaped into a metamaterial may be varied by varying acoustic waves emitted by acoustic sources 210 and by varying the energy emitted by energy source 240. By changing the frequency or amplitude of acoustic waves emitted from each acoustic source 210, the properties of a plasma metamaterial 220 may be changed by changing the structure of plasma 220 caused by the standing wave pattern created by the interaction of acoustic waves produced by each acoustic source 210. By changing the energy emitted by energy source 240, the density of a plasma metamaterial 220 may be changed. For example, the index of refraction or the frequency of electromagnetic radiation with which plasma metamaterial 220 may interact may be changed by changing the energy emitted by energy source 240. The structure and function of the plasma metamaterial 220 may be changed by changing the acoustic waves produced by each acoustic source 210.

In other embodiments, an object may be placed in contact with plasma 220. In such embodiments, plasma 220 may act on the surface of the object in a variety of ways. Examples of how a plasma may interact with an object placed in contact with the plasma include applying a coating to surfaces of the object with which plasma 220 is in contact, or etching the surface of an object with which plasma 220 is in contact. For example, by shaping a plasma used in processes such as plasma vapor deposition or plasma polymerization with acoustic waves produced by acoustic sources 210, the plasma could be shaped to contact only certain areas of an object placed in chamber 230.

In some embodiments, plasma formation and shaping inside of chamber 230 may be controlled by computer system 290. Computer system 290 may be any suitable computer system in any suitable physical form. In general, computer system 290 may store one or more digital representations desired shape and properties, such as temperature and density, of plasma 220 and provide chamber 230 with information to form and shape plasma 220. For example, computer system 290 may store a mathematical model of plasma 220 and provide instructions to acoustic sources 210 and energy sources 240 of chamber 230 based on measurements from sensors 260 to form and shape plasma 220.

Computer system 290 may be integrated into chamber 230, connected to chamber 230, or be multiple computer systems both integrated into chamber 230 and separate from chamber 230. As an example and not by way of limitation, computer system 290 may be a virtual machine (VM), an embedded computer system, a system-on-chip (SOC), a single-board computer system (SBC) (e.g., a computer-on-module (COM or a system-on-module (SOM)), a desktop computer system, a laptop or notebook computer system, a mainframe, a mesh of computer systems, a server, an application server, or a combination of two or more of these. Where appropriate, computer system 290 may include one or more computer systems 290; be unitary or distributed; span multiple locations; span multiple machines; or reside in a cloud, which may include one or more cloud components in one or more networks. Where appropriate, one or more computer systems 150 may perform without substantial spatial or temporal limitation one or more steps of one or more methods described or illustrated herein. As an example and not by way of limitation, one or more computer systems 290 may perform in real time or in batch mode one or more step of one or more methods described or illustrated herein. One or more computer systems 290 may perform at different times or at different locations one or more steps of one or more methods described or illustrated herein, where appropriate. A particular embodiment of computer system 290 is described in more detail below in reference to FIG. 3.

Figure 2B:
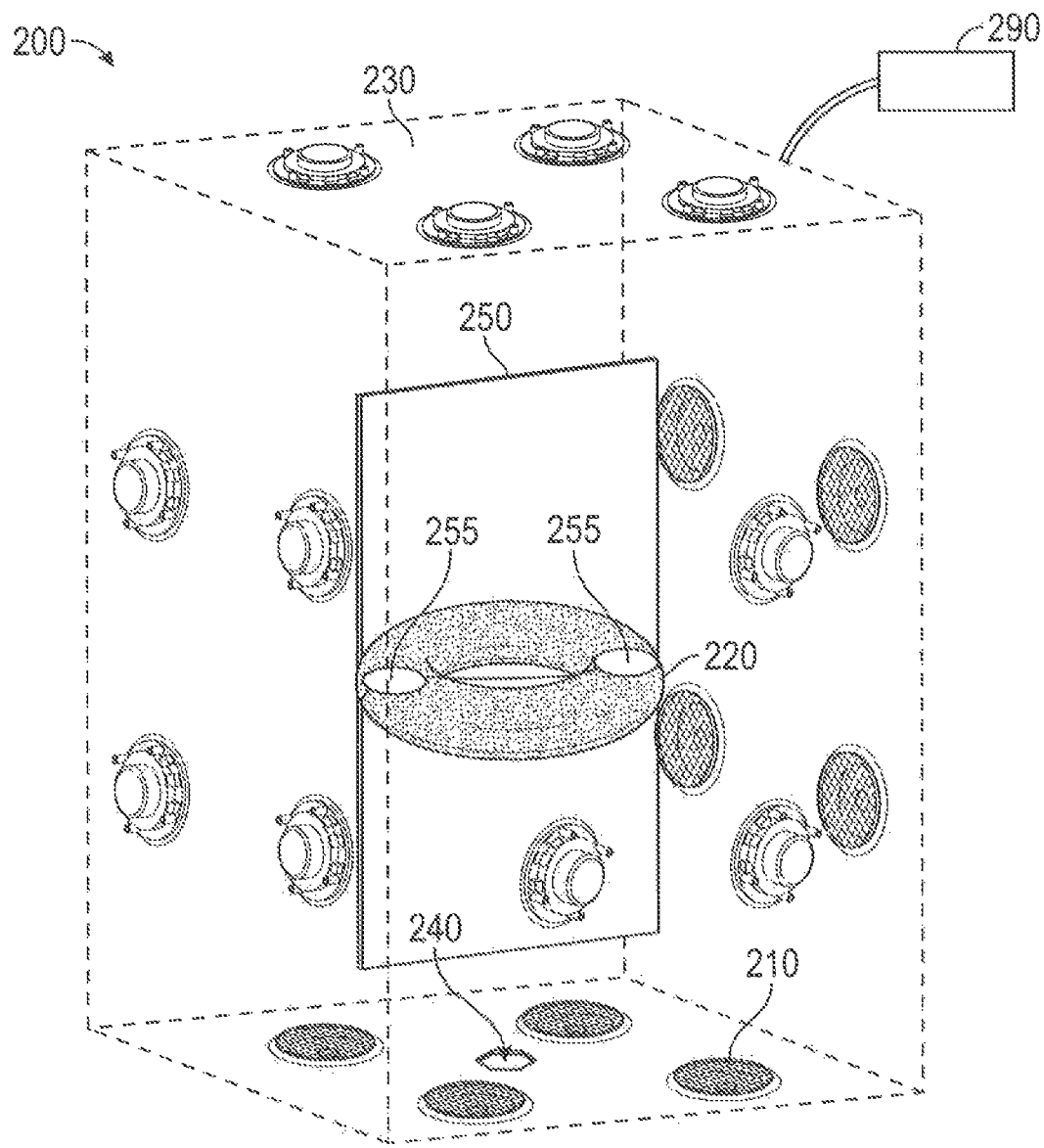
FIG. 2B illustrates an object placed in contact with a plasma shaped in three dimensions, according to certain embodiments.

FIG. 2B illustrates an object 250 placed in contact with plasma 220, according to certain embodiments. In the illustrated example, plasma 220, formed into a torus, contacts object 250 at points of intersection 255 where the plasma torus 220 intersects object 250. In the illustrated example, this intersection is two circles on each side of plate shaped object 250. However, plasma 220 may be shaped into any arbitrary structure by acoustic waves generated by acoustic sources 210, and therefore could be shaped to contact a complexly shaped object 250 at any number of desired areas.

In certain embodiments plasma 220 may be configured to apply a coating at points of intersection 255 with object 250. For example, by plasma vapor deposition or plasma polymerization. In other embodiments, plasma 220 may be configured to etch object 250 at points of intersection 255.

Figure 2C:
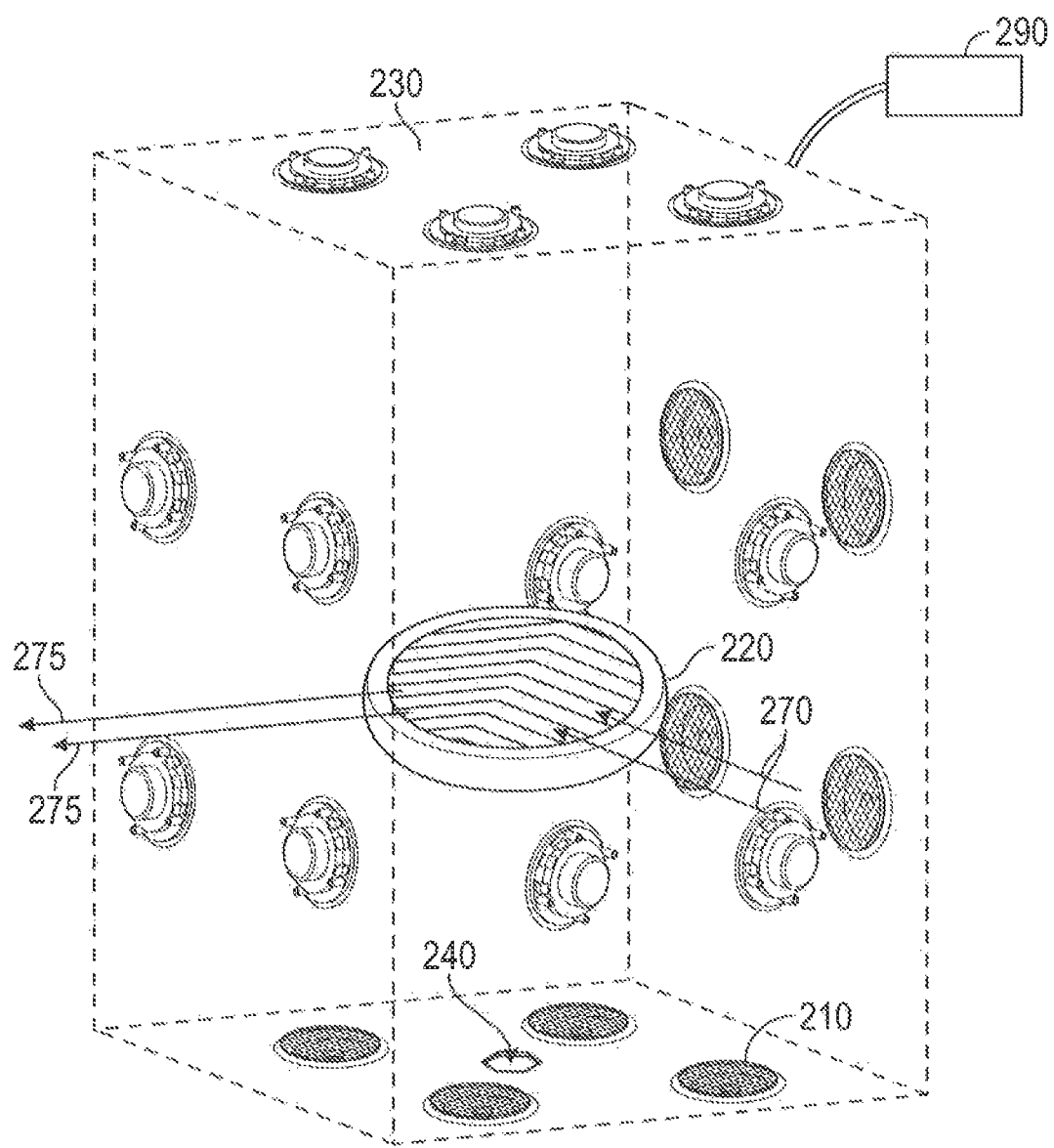
FIG. 2C illustrates an interaction between electromagnetic radiation and a plasma metamaterial shaped in three dimensions by acoustic waves, according to certain embodiments.

FIG. 2C illustrates an embodiment in which non-ionizing electromagnetic radiation 270 is directed into plasma 220 after the plasma has been formed. Non-ionizing electromagnetic radiation 270 may be any form of electromagnetic energy, including but not limited to, radio waves, microwaves, infrared light, or visible light. In certain embodiments, plasma 220 may be shaped as a metamaterial and configured to steer or focus non-ionizing electromagnetic radiation 270 applied to plasma 220.

In the embodiment illustrated in FIG. 2C, plasma 220 is shaped to steer non-ionizing electromagnetic radiation 270 at a 90 degree angle to the direction from which non-ionizing electromagnetic radiation 270 enters into plasma 220. In this embodiment, non-ionizing electromagnetic radiation 270 exiting plasma 220 is illustrated as non-ionizing electromagnetic radiation 275. In other embodiments, plasma 220 may be shaped into a metamaterial capable of steering non-ionizing electromagnetic radiation 270 at any angle. In other embodiments plasma 220 may be shaped into a metamaterial capable of focusing non-ionizing electromagnetic radiation 270 in a manner similar to a lens or series of lenses. In yet other embodiments, plasma 220 may be shaped into a metamaterial capable of separating different frequencies of non-ionizing electromagnetic radiation 270 in a manner similar to a prism or a filter.

Figure 3:
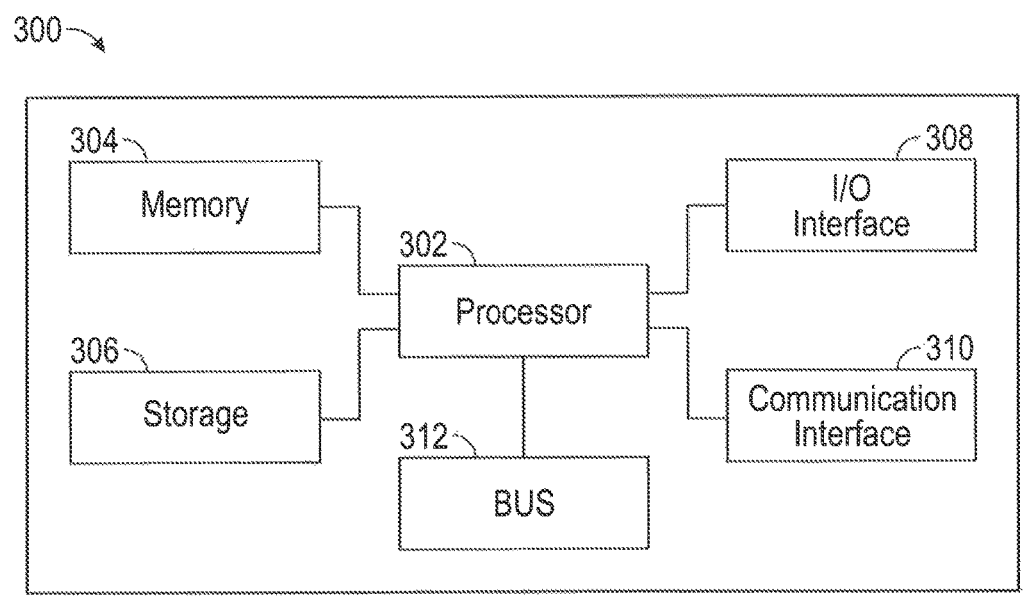
FIG. 3 illustrates an example computer system, according to certain embodiments.

FIG. 3 illustrates an example computer system 300. Computer system 300 may be utilized by computer system 290 of FIG. 2. In particular embodiments, one or more computer systems 300 perform one or more steps of one or more methods described or illustrated herein. In particular embodiments, one or more computer systems 300 provide functionality described or illustrated herein. In particular embodiments, software running on one or more computer systems 300 performs one or more steps of one or more methods described or illustrated herein or provides functionality described or illustrated herein. Particular embodiments include one or more portions of one or more computer systems 300. Herein, reference to a computer system may encompass a computing device, and vice versa, where appropriate. Moreover, reference to a computer system may encompass one or more computer systems, where appropriate.

This disclosure contemplates any suitable number of computer systems 300. This disclosure contemplates computer system 300 taking any suitable physical form. As example and not by way of limitation, computer system 300 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 300 may include one or more computer systems 300; be unitary or distributed; span multiple locations; span multiple machines; span multiple data centers; or reside in a cloud, which may include one or more cloud components in one or more networks. Where appropriate, one or more computer systems 300 may perform without substantial spatial or temporal limitation one or more steps of one or more methods described or illustrated herein. As an example and not by way of limitation, one or more computer systems 300 may perform in real time or in batch mode one or more steps of one or more methods described or illustrated herein. One or more computer systems 300 may perform at different times or at different locations one or more steps of one or more methods described or illustrated herein, where appropriate.

In particular embodiments, computer system 300 includes a processor 302, memory 304, storage 306, an input/output (I/O) interface 308, a communication interface 310, and a bus 312. Although this disclosure describes and illustrates a particular computer system having a particular number of particular components in a particular arrangement, this disclosure contemplates any suitable computer system having any suitable number of any suitable components in any suitable arrangement.

In particular embodiments, processor 302 includes hardware for executing instructions, such as those making up a computer program. As an example and not by way of limitation, to execute instructions, processor 302 may retrieve (or fetch) the instructions from an internal register, an internal cache, memory 304, or storage 306; decode and execute them; and then write one or more results to an internal register, an internal cache, memory 304, or storage 306. In particular embodiments, processor 302 may include one or more internal caches for data, instructions, or addresses. This disclosure contemplates processor 302 including any suitable number of any suitable internal caches, where appropriate. As an example and not by way of limitation, processor 302 may include one or more instruction caches, one or more data caches, and one or more translation lookaside buffers (TLBs). Instructions in the instruction caches may be copies of instructions in memory 304 or storage 306, and the instruction caches may speed up retrieval of those instructions by processor 302. Data in the data caches may be copies of data in memory 304 or storage 306 for instructions executing at processor 302 to operate on; the results of previous instructions executed at processor 302 for access by subsequent instructions executing at processor 302 or for writing to memory 304 or storage 306; or other suitable data. The data caches may speed up read or write operations by processor 302. The TLBs may speed up virtual-address translation for processor 302. In particular embodiments, processor 302 may include one or more internal registers for data, instructions, or addresses. This disclosure contemplates processor 302 including any suitable number of any suitable internal registers, where appropriate. Where appropriate, processor 302 may include one or more arithmetic logic units (ALUs); be a multi-core processor; or include one or more processors 302. Although this disclosure describes and illustrates a particular processor, the disclosure contemplates any suitable processor.

In particular embodiments, memory 304 includes main memory for storing instructions for processor 302 to execute or data for processor 302 to operate on. As an example and not way of limitation, computer system 300 may load instructions from storage 306 or another source (such as, for example, another computer system 300) to memory 304. Processor 302 may then load the instructions from memory 304 to an internal register or internal cache. To execute the instructions, processor 302 may retrieve the instructions from the internal register or internal cache and decode them. During or after execution of the instructions, processor 302 may write one or more results (which may be intermediate or final results) to the internal register or internal cache. Processor 302 may then write one or more of those results to memory 304. In particular embodiments, processor 302 executes only instructions in one or more internal registers or internal caches or in memory 304 (as opposed to storage 306 or elsewhere) and operates only on data in one or more internal registers or internal caches or in memory 304 (as opposed to storage 306 or elsewhere). One or more memory buses (which may each include an address bus and a data bus) may couple processor 302 to memory 304. Bus 312 may include one or more memory buses, as described below. In particular embodiments, one or more memory management units (MMUs) reside between processor 302 and memory 304 and facilitate accesses to memory 304 requested by processor 302. In particular embodiments, memory 304 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 304 may include one or more memories 304, where appropriate. Although this disclosure describes and illustrates particular memory, this disclosure contemplates any suitable memory.

In particular embodiments, storage 306 includes mass storage for data or instructions. As an example and not by way of limitation, storage 306 may include a hard disk drive (HDD), a floppy disk drive, a flash memory, an optical disc, a magneto-optical disc, magnetic tape, or a Universal Serial Bus (USB) drive or a combination of two or more of these. Storage 306 may include removable or non-removable (or fixed) media, where appropriate. Storage 306 may be internal or external to computer system 300, where appropriate. In particular embodiments, storage 306 is non-volatile, sold-state memory. In particular embodiments, storage 306 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 306 taking any suitable physical form. Storage 306 may include one or more storage control units facilitating communication between processor 302 and storage 306, where appropriate. Where appropriate, storage 306 may include one or more storages 306. Although this disclosure describes and illustrates particular storage, this disclosure contemplates any suitable storage.

In particular embodiments, I/O interface 308 includes hardware, software, or both, providing one or more interfaces for communication between computer system 300 and one or more I/O devices. Computer system 300 may include one or more of these I/O devices, where appropriate. One or more of these I/O devices may enable communication between a person and. computer system 300.

As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 308 for them. Where appropriate, I/O interface 308 may include one or more device or software drivers enabling processor 302 to drive one or more of these I/O devices. I/O interface 308 may include one or more I/O interfaces 308, where appropriate. Although this disclosure describes and illustrates a particular I/O interface, this disclosure contemplates any suitable I/O interface.

In particular embodiments, communication interface 310 includes hardware, software, or both providing one or more interfaces for communication (such as, for example, packet-based communication) between computer system 300 and one or more other computer systems 300 or one or more networks. As an example and not by way of limitation, communication interface 310 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 310 for it. As an example and not by way of limitation, computer system 300 may communicate with an ad hoc network, a personal area network (PAN), a local area network (LAN), a wide area network (WAN), a metropolitan area network (MAN), or one or more portions of the Internet or a combination of two more of these. One or more portions of one or more of these networks may be wired or wireless. As an example, computer system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 300 may include any suitable communication interface 310 for any of these networks, where appropriate. Communication interface 310 may include one or more communication interfaces 310, where appropriate. Although this disclosure describes and illustrates a particular communication interface, this disclosure contemplates any suitable communication interface.

In particular embodiments, bus 312 includes hardware, software, or both coupling components of computer system 300 to each other. As an example and not by way of limitation, bus 312 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 312 may include one or more buses 312, where appropriate. Although this disclosure describes and illustrates a particular bus, this disclosure contemplates any suitable bus or interconnect.

The components of computer system 300 may be integrated or separated. In some embodiments, components of computer system 300 may each be housed within a single chassis. The operations of computer system 300 may be performed by more, fewer, or other components. Additionally, operations of computer system 300 may be performed using any suitable logic that may comprise software, hardware, other logic, or any suitable combination of the preceding.

Figure 4:
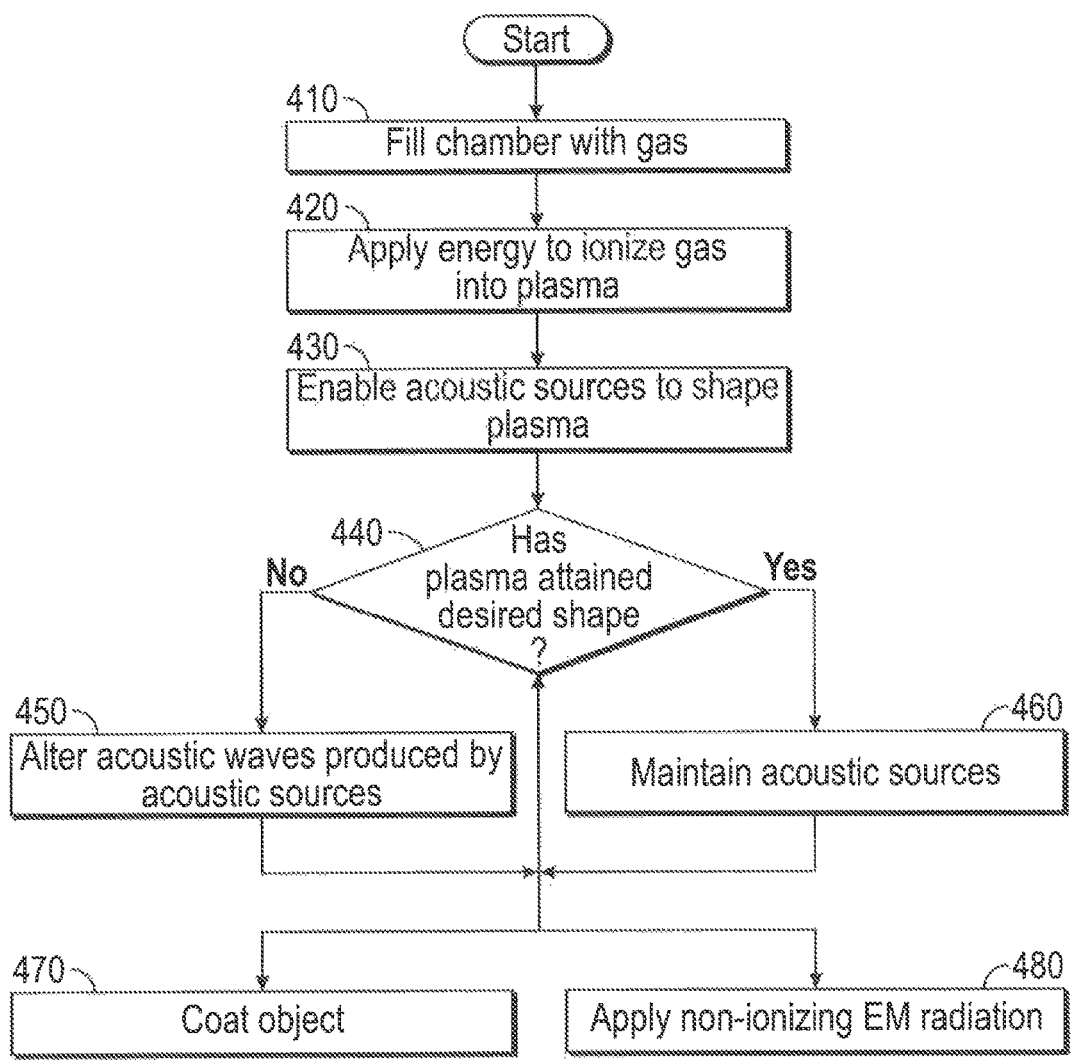
FIG. 4 illustrates a method for forming and shaping a plasma, according to certain embodiments.

FIG. 4 illustrates a method 400 for forming and shaping a plasma, according to certain embodiments. Method 400 may be carried out by an apparatus for containing, forming, and shaping a plasma, such as apparatus 200 of FIG. 2. Method 400 begins at step 410, where a chamber, such as chamber 230 of FIG. 2, is filled with a gas. At step 410, chamber 230 may be filled with a gas to a desired pressure. In some embodiments, the interior of chamber 230 may be filled to a pressure greater than or equal to 1 millitorr (mTorr) and less than or equal to 1000 torr at step 410.

At step 420, electromagnetic radiation may be applied to the gas occupying chamber 230 to ionize the gas, forming a plasma. In some embodiments, electromagnetic radiation may be supplied by an energy source such as energy source 240 of FIG. 2. In some embodiments, the electromagnetic energy applied to the gas may be radio frequency (RF) energy. In other embodiments, the electromagnetic energy applied to the gas may be may be high energy microwave radiation. In other embodiments, the electromagnetic energy applied to the gas may be an electron beam. In some embodiments, the electromagnetic energy may be applied to the gas from more than one source or from multiple directions.

After the plasma has been formed at step 420, acoustic waves may be applied to the plasma at step 430. The acoustic waves may be generated by a plurality of acoustic sources 210 as illustrated in FIG. 2. Application of acoustic waves to the plasma may form the plasma into a shape. Acoustic waves produced by each acoustic source 210 may be configured to produce a standing wave pattern when the acoustic waves interact with each other. This standing wave pattern shapes the plasma and may cause the plasma to form a shape having areas of higher density and areas of lower density. In some embodiments, the acoustic waves may be tuned so as to create a plasma having the properties of a metamaterial.

Step 430 may occur prior to step 420, in certain embodiments. Acoustic waves may be applied to the gas inside of chamber 230 prior to a plasma being formed at step 420. In such embodiments, the acoustic waves applied at step 430 may shape the neutral gas into the desired shape prior to ionization and formation of the plasma at step 420.

At step 440, the apparatus for producing and shaping the plasma may determine if the plasma has reached the desired shape. If the plasma has not reached the desired shape, one or more acoustic sources 210 may alter the acoustic waves being produced to induce a change in the shape of the plasma. For example, computer system 290 of FIG. 2 may use information obtained from sensors 260 to determine of plasma 220 has reached a desired shaped. If computer system 290 determines that plasma 220 has not reached the desired shape, or deviates from the desired shape by a specified amount, then computer system 290 may instruct one or more acoustic sources 210 to change the acoustic waves those acoustic sources are producing.

In some embodiments, the acoustic sources 210 may constantly alter acoustic waves in order to maintain a shape in the plasma, as the plasma may naturally dynamically change shape. In some embodiments, the acoustic waves may be altered based on the plasma's deviation from a desired shape using a feedback loop controlled by computer 290. In certain embodiments, the acoustic waves may be altered to change the shape of the plasma from a first shape to a second desired shape. When the plasma has reached its desires shape, the acoustic waves may be maintained at a constant level until the plasma deviates from the desired shape by a set amount, in certain embodiments.

In some embodiments, at step 470, an object may be placed in contact with the plasma maintained in step 440. For example, an object such as object 250 of FIG. 2B may be placed in contact with plasma 220. Plasma 220 may be configured to apply a coating to object 250 or may be configured to etch object 250. In some embodiments, the object may be placed in chamber 230 prior to formation and shaping plasma 220 at step 430 and step 440.

In other embodiments, at step 480, non-ionizing electromagnetic radiation may be applied to the plasma maintained at step 440. For example, if plasma 220 is shaped as a metamaterial, radio frequency waves applied to plasma 220 may be guided or focused by plasma 220 at step 480 as illustrated in FIG. 2C.

Modification, additions, or omissions may be made to the methods described herein without departing from the scope of the invention. For example, the steps may be combined, modified, or deleted where appropriate, and additional steps may be added. Additionally, the steps may be performed in any suitable order without departing from the scope of the present disclosure.

Although the present invention has been described with several embodiments, a myriad of changes, variations, alterations, transformations, and modifications may be suggested to one skilled in the art, and it is intended that the present invention encompass such changes, variations, alterations, transformations, and modifications as fall within the scope of the appended claims.

What is claimed is:

1. An apparatus for producing a plasma having a three dimensional shape comprising:
    a chamber filled with a gas;
    an energy source operable to provide energy to ionize the gas in the chamber to form a plasma;
    a plurality of sensors operable to measure one or more properties of the plasma; and
    a plurality of acoustic sources capable of producing acoustic waves, wherein the acoustic waves produced by each of the plurality of acoustic sources interact to create a standing wave pattern forming a three dimensional shape in the plasma; and
    wherein the apparatus is configured to direct electromagnetic radiation through the plasma and the electromagnetic radiation is guided by the three dimensional shape.

2. The apparatus of claim 1, wherein the energy source is a radio frequency source or an electron beam.

3. The apparatus of claim 1, wherein the gas in the chamber has a pressure between 1 millitorr and 1000 torr.

4. The apparatus of claim 1, wherein the plasma modifies the vacuum permittivity for an electromagnetic frequency.

5. The apparatus of claim 1, wherein the plurality of acoustic sources are operable to change the acoustic waves to maintain a three dimensional shape in the plasma.

6. The apparatus of claim 1, wherein the plurality of acoustic sources are operable to change the acoustic waves to change a three dimensional shape in the plasma.

7. The apparatus of claim 1, wherein the apparatus is operable to apply a coating to an object placed in the chamber, the coating being applied to areas of the object according to the three-dimensional shape of the plasma.

8. A method for producing a three dimensional shape in a plasma comprising:
    filling a space with a gas;
    ionizing the gas with a radio frequency source to form a plasma;
    directing acoustic waves into the plasma from a plurality of acoustic sources, wherein the acoustic waves from each of the plurality of acoustic sources interact to create a standing wave pattern forming a three dimensional shape in the plasma; and
    directing electromagnetic radiation through the plasma, wherein the electromagnetic radiation is guided by the three dimensional shape.

9. The method of claim 8, wherein the plasma modifies the vacuum permittivity for an electromagnetic frequency.

10. The method of claim 8, wherein the gas has a pressure between 1 millitorr and 1000 torr.

11. The method of claim 8, further comprising changing the acoustic waves from each of the plurality of acoustic sources to maintain the three dimensional shape.

12. The method of claim 8, further comprising changing the acoustic waves from each of the plurality of acoustic sources to change the three dimensional shape.

13. The method of claim 8, further comprising applying a coating to an object placed in the plasma chamber, the coating being applied to areas of the object according to the three-dimensional shape of the plasma.

14. A system for directing electromagnetic radiation comprising:
    a chamber;
    a plasma contained within the chamber;
    a plurality of acoustic sources;
    a portion of the chamber configured to allow electromagnetic radiation to enter the chamber; and
    a portion of the chamber configured to allow electromagnetic radiation to exit the chamber;
    wherein:
        the plasma is formed into a plasma metamaterial by acoustic waves generated by the plurality of acoustic sources; and
        the plasma metamaterial is configured by the acoustic waves to direct electromagnetic radiation entering the chamber through the portion of the chamber configured to allow electromagnetic radiation to enter the chamber to the portion of the chamber configured to allow electromagnetic radiation to exit the chamber.

15. The system of claim 14, wherein the plasma has a pressure between 1 millitorr and 1000 torr.

16. The system of claim 14, wherein the plasma modifies the vacuum permittivity for an electromagnetic frequency.

17. The system of claim 14, wherein the plasma metamaterial is configured to direct microwaves.

18. The system of claim 14, wherein the plasma metamaterial is a three dimensional plasma metamaterial.

* * * * *